United States Patent
Yan et al.

(10) Patent No.: US 9,663,446 B2
(45) Date of Patent: May 30, 2017

(54) PROCESS FOR FORMING A PRIMARY, A SECONDARY OR A TERTIARY AMINE VIA A DIRECT AMINATION REACTION

(71) Applicants: RHODIA OPERATIONS, Paris (FR); Centre National De La Recherche Scientifique, Paris (FR)

(72) Inventors: Zhen Yan, Shanghai (CN); Mohamad Ousmane, Shanghai (CN); Marc Pera-Titus, Shanghai (CN); Floryan DeCampo, Shanghai (CN)

(73) Assignees: RHODIA OPERATIONS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/027,727

(22) PCT Filed: Oct. 15, 2013

(86) PCT No.: PCT/CN2013/085253
§ 371 (c)(1),
(2) Date: Apr. 7, 2016

(87) PCT Pub. No.: WO2015/054828
PCT Pub. Date: Apr. 23, 2015

(65) Prior Publication Data
US 2016/0244401 A1    Aug. 25, 2016

(51) Int. Cl.

| | |
|---|---|
| *C07C 209/18* | (2006.01) |
| *C07C 209/16* | (2006.01) |
| *C07D 215/06* | (2006.01) |
| *C07D 307/14* | (2006.01) |
| *C07D 307/52* | (2006.01) |
| *B01J 23/63* | (2006.01) |
| *B01J 35/10* | (2006.01) |
| *B01J 37/02* | (2006.01) |

(52) U.S. Cl.
CPC ............. *C07C 209/18* (2013.01); *B01J 23/63* (2013.01); *B01J 35/1019* (2013.01); *B01J 37/0201* (2013.01); *C07C 209/16* (2013.01); *C07D 215/06* (2013.01); *C07D 307/14* (2013.01); *C07D 307/52* (2013.01)

(58) Field of Classification Search
None
See application file for complete search history.

(56) References Cited

U.S. PATENT DOCUMENTS

| | | | | |
|---|---|---|---|---|
| 4,532,324 | A | * 7/1985 | Renken | ..................... B01J 23/83 544/106 |
| 4,942,261 | A | 7/1990 | Ishimura et al. | |
| 6,111,141 | A | * 8/2000 | Eller | ..................... C07C 209/26 564/473 |

FOREIGN PATENT DOCUMENTS

| | | |
|---|---|---|
| EP | 0300852 A1 | 1/1989 |
| EP | 0388567 A1 | 9/1990 |
| WO | WO 2010018570 A1 | 2/2010 |

OTHER PUBLICATIONS

Li, et al.—Preparation and Properties of Ceria Supported Palladium Catalyst (2013) Experiment Science and Technology, vol. 11, No. 1, 6-7 and 186.
Bahn et al—The Catalytic Amination of Alcohols (2011) ChemCatChem, 3, 1853-1864 (12 pages).
Guillena, et al.—Hydrogen Autotransfer in the N-Alkylation of Amines and Related Compounds using Alcohols and Amines as Electrophiles (2009) Chem. Rev. 2010, 110, 1611-1641 (31 pages).
Nixon, et al.—Transition metal catalysed reactions of alcohols using borrowing hydrogen methodology (2009) Dalton Trans, 753-762 (10 pages).
Cano et al.—Impregnated Ruthenium on Magnetite as a a Recyclable Catalyst for the N-Alkylation of Amines, Sulfonamides, Sulfinamides, and Nitroarenes Using Alcohols as Electrophiles by Hydrogen Autotransfer Process (2011) J. Org. Chem. 76, 5547-5557 (11 pages).
Corma et al.—A Bifunctional Pd/MgO Solid Catalyst for the One-Pot Selective N-Monoalkylation of Amines with Alcohols (2010) Chem. Eur. J., 16, 254-260 (7 pages).
Zhang et al.—Palladium catalyzed N-alkylation of amines with alcohols (2011) Tetrahedron Letters 52, 1334-1338 (5 pages).
Brunauer et al.—Adsorption of Gases in Multimolecular Layers (1938) The Journal of the American Chemical Society, 60, 309-319 (11 pages).
Han et al.—Kinetics of ethylene combustion in the synthesis of vinyl acetate over a Pd/SiO$_2$ catalyst (2004) Journal of Catalysis 224, 60-68 (9 pages).

* cited by examiner

*Primary Examiner* — Clinton Brooks

(57) ABSTRACT

Disclosed is a process for preparing a primary, a secondary or a tertiary amine via the direct amination of an alcohol in the presence of a catalyst. The catalyst is composed of palladium or a palladium compound and a cerium oxide supporter.

14 Claims, No Drawings

PROCESS FOR FORMING A PRIMARY, A SECONDARY OR A TERTIARY AMINE VIA A DIRECT AMINATION REACTION

This application is a U.S. national phase entry under 35 U.S.C. §371 of International Application No. PCT/CN2013/085253 filed on Oct. 15, 2013, the entirety of which is being incorporated herein by reference for all purposes.

The present invention concerns a process for forming a primary, a secondary or a tertiary amine, via the direct amination of an alcohol by using a catalyst composed of a cerium oxide support and comprising at least a palladium compound.

PRIOR ART

Amines are of significant importance to the chemical industry. These synthetic amines are used as solvents, agrochemicals, pharmaceuticals, detergents, fabric softeners, flotation agents, corrosion inhibitors, antistatic additives, lubricants, polymers, varnishes, and dyes. A variety of procedures have been developed for the synthesis of organic amines, such as hydroamination, reduction of nitriles and nitro compounds, or reductive amination (S. Bähm, S. Imm, L. Neubert, M. Zhang, H. Neumann, M. Beller, ChemCatChem 3 (2011) 1853). The feedstocks for many of these processes are ketones, aldehydes, nitriles, carboxylic acids, alkyl halides or alkenes.

With the development of many biomass-based processes and technologies, alcohols become a potential and promising source for the chemical industrial, including the synthesis of amines.

Direct amination of alcohols is a very attractive pathway to prepare amines because water is the only byproduct for this process. Various techniques have been described in the literature but usually require stringent conditions such as high temperature or high pressure of hydrogen.

The reaction between alcohol and ammonia is the most common method for the manufacture of lower alkyl amines. Dehydrogenation catalysts based on nickel, cobalt, iron and copper are used and the reaction typically takes place at 0.5-20 MPa at temperatures of 100-250° C. Hydrogen is added to the mixture to maintain the activity of the metal surface of the catalyst.

Generally, aldehydes and ketones are used in preference to alcohols as raw materials for amine synthesis. The reductive amination reaction is usually described to proceed in two stages, as shown below:

$$RHC{=}O+NH_3 \rightarrow RHC{=}NH+H_2O$$

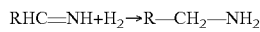

Hydrogenation of nitriles is also used to produce some amines. Hydrogen is consumed stoichiometrically in such types of processes.

Amines are also prepared by the reaction of olefins with hydrocyanic acid followed by reduction or the reaction of alkyl halides with ammonia. These processes usually involve hazardous reagents such as HCN, or generate hazardous byproducts such as HCl. The neutralization of HCl using a base generates 2 eq. NaCl per 1 eq. of diamine generated, making the process environmentally unfriendly.

As a shift from fossil feedstock, it appears that the use of biomass as a feedstock will lead to the production of many different alcohols.

Therefore, direct amination of alcohols with ammonia or amines with water as the only byproduct becomes a very important pathway for the synthesis of amines:

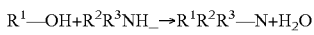

($R^1$=alkyl/$R^2$, $R^3$=H or alkyl)

There have been significant amount of studies in the literature on the direct amination of alcohols, such as G. Guillena, D. J. Ramón, M. Yus, Chem. Ver. 110 (2009) 1611 and T. D. Nixon, M. K. Whittlesey, J. M. J. Williams, Dalton Trans 0 (2009) 753. The most studied systems for the synthesis of amines from alcohols are based on homogeneous organometallic catalysts. Ru and Ir-based complexes are the most widely used and have been shown to have good to excellent yields for the amination of a variety of alcohols. So far, no homogeneously catalyzed alcohol amination has been employed on industrial scale as mentioned in S. Bähn, S. Imm, L. Neubert, M. Zhang, H. Neumann, M. Beller, ChemCatChem 3 (2011) 1853.

Heterogeneously catalyzed amination of alcohols has also been reported, although less common compared to the homogeneously counterpart. The group of Mizuno investigated heterogeneous ruthenium catalysts for the N-alkylation of primary and secondary amines with primary alcohols. Applying the supported ruthenium hydroxide catalyst Ru(OH)x/$Al_2O_3$, anilines were selectively N-monoalkylated to give the following secondary amine products:

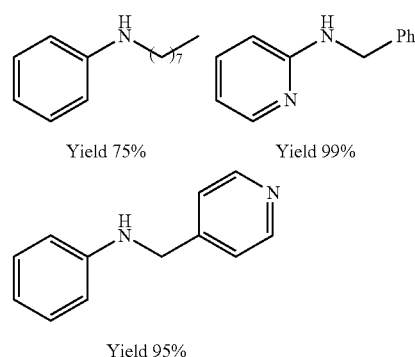

Cano and co-workers reported impregnated ruthenium on magnetite to catalyze the N-alkylation of aromatic amines with primary benzylic alcohols to give secondary amines (R. Cano, D. J. Ramón, M. Yus, J. Org. Chem. 76 (2011) 5547).

Pd catalysts supported on certain oxides also show promising performance for the N-alkylation of amines with alcohols. Corma et al. reported that a Pd/MgO catalyst is highly selective for the monoalkylation of aniline with benzyl alcohol (A. Corma, T. Rodenas, M. J. Sabater, Chem.-Eur. J. 16 (2010) 254). Shi et al. showed that an iron oxide-supported Pd catalysts exhibits high yields for reactions of amines and alcohols with various structures (Y. Zhang, X. Qi, X. Cui, F. Shi, Y. Deng, Tetrahedron Lett. 52 (2011) 1334).

Invention

It appears now that it's perfectly possible to produce a primary, a secondary or a tertiary amine, via the direct amination of an alcohol by using a catalyst composed of a cerium oxide support and comprising at least a palladium compound; said catalyst showing much higher activity and selectivity than conventional amination catalysts, including Pd catalysts supported on other materials, such as alumina, silica, activated carbon, and titania. It also appears that this catalyst is stable during the direct amination reaction of the invention and both the activity and selectivity of said catalyst are the same with fresh catalyst or yet used catalyst.

The present invention concerns then a process to produce a primary, a secondary or a tertiary amine, comprising at least reacting of:
1) a first reactant being a compound having at least one primary or secondary hydroxyl function, with
2) a second reactant being $NH_3$ or a compound having at least one primary or secondary amine function,
and at least in the presence of a catalyst composed of a cerium oxide support and comprising at least a palladium compound.

Definitions

Throughout the description, including the claims, the term "comprising one" should be understood as being synonymous with the term "comprising at least one", unless otherwise specified, and "between" should be understood as being inclusive of the limits.

As used herein, the term "hydrocarbon group" refers to a group consisting of carbon atoms and hydrogen atoms, which group may be saturated or unsaturated, linear, branched or cyclic, aliphatic or aromatic. Hydrocarbon groups of the present invention may be alkyl groups, alkenyl groups, alkynyl groups, aryl groups and heterocyclic groups.

As used herein, "alkyl" groups include saturated hydrocarbons having one or more carbon atoms, including straight-chain alkyl groups, such as methyl, ethyl, propyl, butyl, pentyl, hexyl, heptyl, octyl, nonyl, decyl, cyclic alkyl groups (or "cycloalkyl" or "alicyclic" or "carbocyclic" groups), such as cyclopropyl, cyclopentyl, cyclohexyl, cycloheptyl, and cyclooctyl, branched-chain alkyl groups, such as isopropyl, tert-butyl, sec-butyl, and isobutyl, and alkyl-substituted alkyl groups, such as alkyl-substituted cycloalkyl groups and cycloalkyl-substituted alkyl groups. The term "aliphatic group" includes organic moieties characterized by straight or branched-chains, typically having between 1 and 22 carbon atoms. In complex structures, the chains may be branched, bridged, or cross-linked. Aliphatic groups include alkyl groups, alkenyl groups, and alkynyl groups.

As used herein, "alkenyl" or "alkenyl group" refers to an aliphatic hydrocarbon radical which can be straight or branched, containing at least one carbon-carbon double bond. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "alkynyl" refers to straight or branched chain hydrocarbon groups having at least one triple carbon to carbon bond, such as ethynyl.

The term "aryl group" includes unsaturated and aromatic cyclic hydrocarbons as well as unsaturated and aromatic heterocycles containing one or more rings. Aryl groups may also be fused or bridged with alicyclic or heterocyclic rings that are not aromatic so as to form a polycycle, such as tetralin. An "arylene" group is a divalent analog of an aryl group. Aryl groups can also be fused or bridged with alicyclic or heterocyclic rings which are not aromatic so as to form a polycycle.

The term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups, such as pyrrolyl, pyridyl, isoquinolyl, quinolyl, purinyl, and furyl, may have aromatic character, in which case they may be referred to as "heteroaryl" or "heteroaromatic" groups.

Aryl and heterocyclic including heteroaryl groups may also be substituted at one or more constituent atoms. Examples of heteroaromatic and heteroalicyclic groups may have 1 to 3 separate or fused rings with 3 to about 8 members per ring and one or more N, O, or S heteroatoms. In general, the term "heteroatom" includes atoms of any element other than carbon or hydrogen, preferred examples of which include nitrogen, oxygen, sulfur, and phosphorus. Heterocyclic groups may be saturated or unsaturated or aromatic.

DETAILS OF THE INVENTION

It is well known in the art that cerium oxide may be used as a catalyst or a catalyst support. Several cerium oxides may be used for this purpose.

Cerium oxide of the present invention may provide a specific surface of at least 190 $m^2/g$, notably between 200 and 280 $m^2/g$, measured after calcination at a temperature of 350° C. for 2 hours. "Specific surface" notably means the specific B.E.T. surface determined by nitrogen adsorption in accordance with the ASTM D 3663-78 standard established by the BRUNAUER-EMMETT-TELLER method described in "The Journal of American Society, 60, 309 (1938)".

Cerium oxide of the present invention may provide a specific surface of at least 15 $m^2/g$, notably between 20 and 60 $m^2/g$, measured after calcination at a temperature of 800° C. for 2 hours.

Cerium oxide of the present invention may provide a porous volume of greater than 0.1 $cm^3/g$, preferably greater than 0.15 $cm^3/g$, notably between 0.15 and 0.25 $cm^3/g$, at a measurement temperature of 800° C. for 2 hours. The porous volume, which corresponds to pores with a diameter of less than 60 nm, is measured with a mercury porosimeter in accordance with the ASTM D4284-83 standard or using the isotherm nitrogen adsorption method (the above-identified B.E.T. method).

These cerium oxides are notably described in the EP300852 and EP388567 publications.

These cerium oxide supports may be obtained by calcination of a ceric hydroxide in which the cerium hydroxide is subjected to solvothermal treatment before calcination.

These cerium oxide supports may notably be obtained according to the following process consisting of:
preparing a ceric hydroxide by reacting a solution of cerium salt and a base, possibly in the presence of an oxidizing agent, with the amount of the base being such that the pH of the reaction medium is greater than 7; of separating the precipitate obtained, and possibly washing it;
placing the ceric hydroxide in suspension in water or in an aqueous solution of a decomposable base;
heating it in a closed chamber to a temperature and a pressure respectively lower than the critical temperature and the critical pressure of said medium;
cooling the reaction mixture and bringing it to atmospheric pressure;
separating the ceric hydroxide treated in this manner; then calcining it.

Palladium compound of the present invention may be palladium metal itself or any compound comprising palladium such as for example salts or oxides of palladium.

Palladium compounds are preferably chosen in the group consisting of: palladium metal, PdO, $PdO_2$, palladium nitrate, palladium chloride, palladium acetate, palladium acetylacetonate, and palladium hydroxide.

Catalysts composed of a cerium oxide support and comprising at least a palladium compound may be obtained by several know methods such as for example impregnation or co-precipitation, notably incipient wetness impregnation. Several palladium compounds or palladium compound precursors may be used such as for example palladium(II) nitrate dehydrate, palladium chloride, palladium acetate, palladium acetylacetonate, and palladium hydroxide.

Impregnation of an appropriate catalyst support is notably mentioned in Y.-F. Han et al. Journal of Catalysis 224 (2004) 60.

The activation or re-activation of the catalysts may involve a calcination step and/or a reduction step under hydrogen. Notably, the activation of the modified catalysts may involve a calcination step under air or $O_2$ at 300-500° C. for 1-24 hours and a reduction step under hydrogen at the same temperature for 1-6 hours. It is also possible to activate the catalyst of the present invention by reduction in a flow of hydrogen at 300-500° C.

The concentration of palladium compound on cerium oxide may be comprised between 0.1 and 20% by weight, preferably from 0.5 to 10% by weight.

The weight ratio of the catalyst of the present invention to the second reactant may be comprised between 0.05 and 2, preferably from 0.1 to 0.5.

The first reactant of the invention is a compound having at least one primary or secondary hydroxyl function. This compound can notably be a compound comprising two, similar or different, primary or secondary functions. Preferably, the first reactant is a compound comprising one or two primary hydroxyl functions.

This first reactant may notably be a compound of formula (I):

$$R^1—(CH_2—OH)_x \quad (I)$$

Wherein:

x is 1 or 2, and $R^1$ is H or a straight, branched or cyclic hydrocarbon group.

$R^1$ may represent straight, branched or cyclic hydrocarbon group that can be an alkyl, alkenyl, aryl, cycloalkyl or heterocyclic group, eventually comprising one or several heteroatoms such as O, S, F, and N. Preferred groups for $R^1$ may be for example: H, alkyl, cyclic alkane, cyclic alkene, phenyl, furanyl, and tetrahydrofuranyl.

In addition the first reactant may comprise additional functionalities. The additional functionalities may behave as electron donating or electron withdrawing groups. There is no particular limitation on the number of carbon atoms present in the reactant as long as its structure does not prevent the direct amination reaction.

Preferred first reactants of the present invention, such as compounds of formula (I), are chosen in the group consisting of: furfuryl alcohol, 2,5 furandimethanol, 2,5-tetrahydrofuranedimethanol, benzyl alcohol, 1,6-hexanediol, 1,2-cyclohexanediol, 1,4-cyclohexanediol, 1-phenylethanol, 1,7-heptandiol, 1,3-propanediol, 1,4-butanediol, ethylene glycol, and isosorbide.

It has to be noticed that it's perfectly possible to use several first reactant types during the reaction of the present invention.

Concentration of the first reactant may be comprised between 0.001 and 10 $mol.L^{-1}$, when a solvent is used in the reaction medium.

The second reactant of the invention is $NH_3$ or a compound having at least one primary or secondary amine function.

This second reactant may notably be a compound of formula (II):

$$R^2—NH_2 \quad (II)$$

Wherein $R^2$ is H or a straight, branched or cyclic hydrocarbon group $R^2$ may represent straight, branched or cyclic hydrocarbon group that can be an alkyl, alkenyl, aryl, cycloalkyl or heterocyclic group, eventually comprising one or several heteroatoms such as O, S, F, and N. Preferred groups for $R^2$ may be for example: H, alkyl, phenyl, benzyl, cycloalkyl, and cycloalkene.

This second reactant may also be a compound of formula (III):

$$R^3—NH—R^4 \quad (III)$$

Wherein $R^3$ and $R^4$ represent, independently from each other, a straight, branched or cyclic hydrocarbon group, $R^3$ and $R^4$ may together form a cyclic group, which may optionally contain a heteroatom. Said cyclic group may notably be an alicyclic group and/or an aromatic group.

$R^3$ and/or $R^4$ may represent straight, branched or cyclic hydrocarbon group that can be an alkyl, alkenyl, aryl, cycloalkyl or heterocyclic group, eventually comprising one or several heteroatoms such as O, S, F, and N. Preferred groups for $R^3$ and $R^4$ may be for example: alkyl, phenyl, benzyl, cycloalkyl, and cycloalkene. $R^4$ may then form together a cyclic group such as a heterocyclic amine. Cyclic groups formed by $R^3$ and $R^4$ may comprise from 2 to 20 carbon atoms and optionally a heteroatom such as O, S, F, and N.

In addition, the second reactant may comprise additional functionalities. The additional functionalities may behave as electron donating or electron withdrawing groups. There is no particular limitation on the number of carbon atoms present in the reactant as long as its structure does not prevent the direct amination reaction.

Preferred second reactants of the present invention, such as compounds of formula (II), are chosen in the group consisting of: ammonia, phenylamine, n-heptylamine, aniline, methylamine, dimethylamine, and dodecylamine.

Preferred second reactants of the present invention, such as compounds of formula (III), are chosen in the group consisting of: pyrrolidine, pyrrol, pyridine, imidazole, quinoleine tetrahydroquinoleine, aziridine, azirine, and piperidine.

It has to be noticed that it's perfectly possible to use several second reactant types during the reaction of the present invention.

Concentration of the second reactant may be comprised between 0.001 and 10 $mol.L^{-1}$, when a solvent is used in the reaction medium.

The amine obtained according to the process of the present invention may be a primary, a secondary or a tertiary amine, preferably a primary or a secondary amine.

The primary or secondary amine of the present invention may notably be a compound of formula (IV):

$$R^1(CH_2—NHR^2)x \quad (IV)$$

Wherein:

x is 1 or 2, $R^1$ is H or a straight, branched or cyclic hydrocarbon group, and $R^2$ is H or a straight, branched or cyclic hydrocarbon group.

Preferred primary or second amines of the invention, such as compounds of formula (IV), are chosen in the group consisting of: N-phenylbenzylamine (N-benzylaniline), dibenzylamine, N-(1-phenylethyl)aniline, 1-benzyl-1,2,3,4-tetrahydroquinoline, N-(cyclohex-2-en-1-yl)benzenamine, (tetrahydrofuran-2,5-diyl)dimethanamine, (furan-2,5-diyl)dimethanamine, 1,6- hexamethylenediamine, 1,1'-(tetrahydrofuran-2,5 -diyl)bis(N-methylmethylamine), and 1,1'-(tetrahydrofuran-2,5-diyl)bis(N-heptaneaminomethane).

Reaction of the present invention may notably be represented as follows:

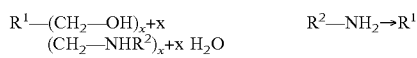

More preferably, reaction of the present invention can be represented as follows:

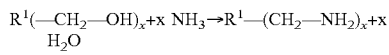

Preferred reactions according to the process of the present invention are the following:
  reaction of benzylalcohol and aniline to produce N-phenyl benzylamine (N-benzylaniline)
  reaction of 2,5-tetrahydrofurandimethanol and ammonia to produce (tetrahydrofuran-2,5-diyl)dimethanamine
  reaction of 2,5-furandimethanol with ammonia to produce (furan-2,5-diyl)dimethanamine
  reaction of 1,6-hexandiol with ammonia to produce 1,6-hexamethylenediamine
  reaction of 1,3-propanediol with ammonia to produce 1,3-propanediamine
  reaction of 1,4-butanediol with ammonia to produce 1,4-butanediamine
  reaction of ethylene glycol with ammonia to produce ethylenediamine-reaction of 2,5-tetrahydrofuranedimethanol with N-heptylamine to produce 1,1'-(tetrahydrofuran-2,5-diyl)bis(N-heptaneaminomethane)

Process of the present invention is carried out at a temperature and for a time sufficient for primary, secondary or tertiary amine, to be produced.

According to a particular embodiment of the present invention, the reaction medium can comprise, notably at the start of the reaction, between 0.1 and 5 molar equivalent of the second reactant for 1 molar equivalent of the first reactant, notably between 0.1 and 1 molar equivalent of the second reactant for 1 molar equivalent of the first reactant in order to selectively produce secondary amine products in the reaction.

The process of the present invention may be carried out without solvent. It is also possible to use a solvent or a combination of solvents for the reaction, notably solvents able to dissolve the first reactant and the second reactant.

Preferred solvents to be used in the process of the invention are apolar solvents, polar aprotic solvents or water.

Apolar solvents are preferably chosen in the group constituting of: hexane, cyclohexane, pentane, cyclopentane, benzene, trimethyl benzene, toluene, xylene, diethyl ether, and chloroform.

Polar aprotic solvents, are preferably chosen in the group constituting of:
  linear ethers, such as diethylether, dimethoxyethane (glyme) or bis(2-methoxyethyl) ether (diglyme) or cyclic ethers, such as tetrahydrofuran, dioxane, methyltetrahydrofuran or dimethyltetrahydrofuran,
  esters, such as methyl or ethyl formate, propylene or ethylene carbonate, or butyrolactones,
  nitriles, acetonitriles, benzonitriles,
  nitrate derivatives, such as nitromethane or nitrobenzene,
  amides, such as dimethylformamide, diethylformamide and N-methylpyrolidone,
  sulfones, such as dimethyl sulfone, tetramethylene sulfone and other sulfolanes.
  sulfoxides, such as DMSO.

A combination of two or more solvents in blend may be used during the reaction of the present invention.

The temperature at which reaction is performed may vary in a large range, but in general it is preferred that the reaction is carried out at a temperature from 0 and 300° C., more preferably between 50 and 200° C., notably between 120 and 180° C. Temperatures may be reached either thermically or by microwave irradiation.

Pressure range of the reaction may be comprised between 1 and 100 bar. Reaction of the present invention may be carried out for a range time comprised between 10 min to 24 hours, preferably between 1 hour and 8 hours.

The reaction may be carried out in the presence of air, hydrogen, or an inert atmosphere such as $N_2$, Ar, $CO_2$ or even $NH_3$. An inert or hydrogen atmosphere is preferred.

This reaction may be conducted in any conventional equipment suitable to effect production of amines. This reaction may be carried out in a continuous or a discontinuous fashion. For example, suitable equipments include a stirred tank or loop reactor.

The reaction may be carried out with one or both reactants in their gas phase. Suitable equipments include a fixed-bed reactor or a fluidized bed reactor. End of reaction may be carried out by stop of the temperature and cooling of the reaction medium, notably air cooling.

The efficiency of the process of the present invention can be monitored by any conventional analytical means, such as Infrared spectroscopy, NMR, Raman spectroscopy, GC, HPLC and SFC.

At the end of the reaction, catalysts may be eventually removed by filtration or centrifugation. Said catalysts may notably be recycled to the reactor.

Amines of interest can be purified by well-known methods of the technical field, such as distillation, crystallization, liquid extraction or extraction with a polymer to adsorb amines The examples provided here further describe and demonstrate embodiments of the present invention. The examples are given solely for the purpose of illustration and are not to be construed as limitation of the present invention.

EXPERIMENTAL PART

The supported Pd catalyst is prepared by incipient wetness impregnation of a high-surface-area ceria (Solvay HSA5, 250 $m^2/g$) with aqueous solution of palladium(II) nitrate dihydrate. In a typical process, 0.15 g of palladium nitrate (~40 wt % Pd) is dissolved into 1.3 mL of deionized water, and the resulting solution was added into 2.94 g of $CeO_2$ slowly while keep stirring. After impregnation for 2 hours, the sample was dried at 120° C. overnight and then calcined in air at 400° C. for 2 hours.

Example 1

The following amination reaction between benzyl alcohol and aniline was used as a probe reaction to compare the performance of the Pd/$CeO_2$ catalyst and other amination catalysts:

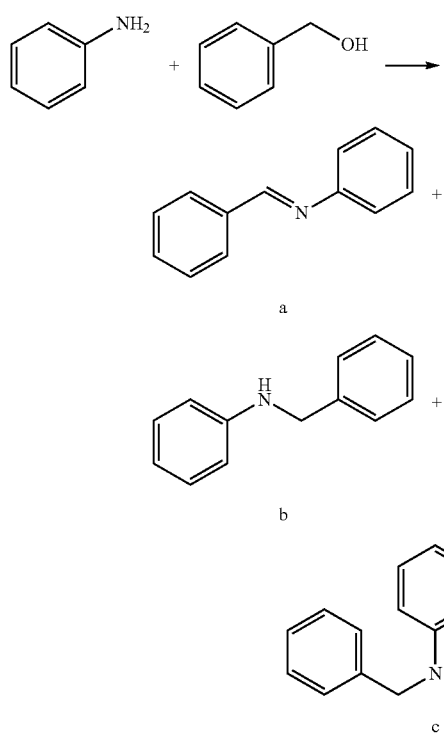

a b c

The secondary amine (product b) is considered as the target product. The results are summarized in the following table.

TABLE 1

Amination of benzyl alcohol with aniline on various catalysts

| Catalyst | Conversion of aniline (%) | Selectivity to secondary amine (%) |
| --- | --- | --- |
| Blank | 0 | — |
| CeO$_2$ (HSA5) | 0 | — |
| Pd/TiO$_2$ (2 wt % Pd*) | 55 | 43 |
| Pd/Al$_2$O$_3$ (2 wt % Pd) | 73 | 56 |
| Pd/C (5 wt % Pd) | 60 | 62 |
| Pd/SiO$_2$ (2 wt % Pd) | 42.6 | 67 |
| Reduced Pt/Al$_2$O$_3$ (2 wt % Pt) | 24 | 88 |
| Reduced Pt/CeO$_2$ (2 wt % Pt) | 14 | 38 |
| Reduced Ni/Al$_2$O$_3$ (2 wt % Ni) | 26 | 66 |
| Pd/CeO$_2$ (2 wt % Pd) | 80 | 91 |
| Reduced Pd/CeO$_2$ (2 wt % Pd) | 90 | >95 |

Reaction conditions: 2 mmol aniline, 6 mmol benzyl alcohol, 60 mg catalyst (24 mg for Pd/C), 160° C., 3 h, N$_2$ atmosphere.
*wt % is expressed with the total weight of catalyst.
"Reduced" means reduction in a flow of hydrogen at 300-500° C. The exact temperature was determined by temperature-programmed reduction.

It appears then that the catalyst of the present invention provided higher conversion and selectivity in the amination reaction in comparison with the other catalysts known in the prior art.

Example 2

The Pd/CeO$_2$ catalysts show high selectivity at a wide range of conditions, including different Pd loadings and at different reaction temperatures, as shown in the following table:

TABLE 2

Effects of Pd loading and reaction temperature on activity and selectivity

| Pd loading (wt %) | Temperature (° C.) | Conversion of aniline (%) | Selectivity to secondary amine (%) |
| --- | --- | --- | --- |
| Blank | 160 | 0 | — |
| 0.0 | 160 | 0 | — |
| 0.5 | 160 | 38 | 91 |
| 2.0 | 160 | 80 | 91 |
| 5.0 | 160 | 92 | >95 |
| 2.0 | 140 | 49 | 91 |
| 2.0 | 120 | 27 | 90 |
| 2.0 | 100 | 16 | 92 |

It appears then that the high selectivity remains over a wide range of reaction conditions and Pd loadings.

Example 3

The Pd/CeO$_7$ catalyst shows excellent stability and reusability, as evidenced by the following two experiments (see Table 1 for reaction conditions). In the first experiment, after 3 hours of reaction, the reactor was cooled to room temperature, the same amount of aniline/benzyl alcohol mixture was added into the reactor, and another 3 hours of reaction was carried out. The post-reaction analysis indicated that the used catalyst has the same activity and selectivity as the fresh catalyst, showing that Pd/CeO$_2$ is stable during the reaction.

In the second experiment, after 3 hours of reaction, the catalyst was washed with ethanol, dried at 100° C., and then calcined at 400° C. The recovered catalyst was tested for the reaction again, and both the activity and selectivity were the same as the fresh catalyst.

The invention claimed is:

1. A process to produce a primary, a secondary or a tertiary amine, the process comprising at least reacting:
    1) a first reactant being a compound having at least one primary or secondary hydroxyl function, with
    2) a second reactant being NH$_3$ or a compound having at least one primary or secondary amine function,
    and at least in the presence of a catalyst composed of a cerium oxide support and comprising at least a palladium compound.

2. The process according to claim 1 wherein the cerium oxide provides a specific surface of at least 190 m$^2$/g, measured after calcination at a temperature of 350° C. for 2 hours.

3. The process according to claim 1 wherein the palladium compound is selected from the group consisting of: palladium metal, PdO, PdO$_2$, palladium nitrate, palladium chloride, palladium acetate, palladium acetylacetonate, and palladium hydroxide.

4. The process according to claim 1 wherein the catalyst is obtained by impregnation or co-precipitation.

5. The process according to of claim 1 wherein the weight ratio of the catalyst to the second reactant is between 0.05 and 2.

6. The process according to claim 1 wherein the first reactant is a compound of formula (I):

$$R^1—(CH_2—OH)_x \tag{I}$$

wherein:
x is 1 or 2, and
R$^1$ is H or a straight, branched or cyclic hydrocarbon group.

7. The process according to claim 1 wherein the first reactant is selected from the group consisting of: furfuryl alcohol, 2,5 furandimethanol, 2,5-tetrahydrofuranedimethanol, benzyl alcohol, 1,6-hexanediol, 1,2-cyclohexanediol, 1,4-cyclohexanediol, 1-phenylethanol, 1,7-heptandiol, 1,3-propanediol, 1,4-butanediol, ethylene glycol, and isosorbide.

8. Process The process according to anyone of claim 1 wherein the second reactant is a compound of formula (II):

$$R^2—NH_2 \tag{II}$$

wherein $R^2$ is H or a straight, branched or cyclic hydrocarbon group.

9. The process according to claim 1 wherein the second reactant is a compound of formula (III):

$$R^3—NH—R^4 \tag{III}$$

wherein $R^3$ and $R^4$ represent, independently from each other, a straight, branched or cyclic hydrocarbon group, $R^3$ and $R^4$ may together form a cyclic group, which may optionally contain a heteroatom.

10. The process according to claim 1 wherein the second reactant is selected from the group consisting of: ammonia, phenylamine, n-heptylamine, aniline, methylamine, dimethylamine, dodecylamine, pyrrolidine, pyrrol, pyridine, imidazole, quinoleine tetrahydroquinoleine, aziridine, azirine, and piperidine.

11. The process according to claim 1 wherein the obtained primary or secondary amine is a compound of formula (IV):

$$R^1(CH_2—NHR^2)x \tag{IV}$$

wherein:
x is 1 or 2,
$R^1$ is H or a straight, branched or cyclic hydrocarbon group, and
$R^2$ is H or a straight, branched or cyclic hydrocarbon group.

12. The process according to claim 1 wherein the obtained primary or secondary amine is selected from the group consisting of: N-phenylbenzylamine (N-benzylaniline), dibenzylamine, N-(1-phenylethyl)aniline, 1-benzyl-1,2,3,4-tetrahydroquinoline, N-(cyclohex-2-en-1-yl)benzenamine, (tetrahydrofuran-2,5-diyl) dimethanamine, (furan-2,5-diyl) dimethanamine, 1,6-hexamethylenediamine, 1,1'-(tetrahydrofuran-2,5-diyl)bis(N-methylethylamine), and 1,1'-(tetrahydrofuran-2,5-diyl)bis(N-heptaneaminomethane).

13. The process according to claim 1 wherein the reaction medium comprises at the start of the reaction, between 0.1 and 5 molar equivalent of the second reactant for 1 molar equivalent of the first reactant.

14. The process according to claim 1 wherein the reaction medium comprises an apolar solvent, a polar aprotic solvent or water.

* * * * *